US006429348B1

(12) United States Patent
Chen et al.

(10) Patent No.: US 6,429,348 B1
(45) Date of Patent: *Aug. 6, 2002

(54) METHOD FOR SELECTIVELY PRODUCING PROPYLENE BY CATALYTICALLY CRACKING AN OLEFINIC HYDROCARBON FEEDSTOCK

(75) Inventors: Tan-Jen Chen, Kingwood, TX (US); S. Mark Davis, Baton Rouge, LA (US); Luc R. M. Martens, Meise; Marcel J. G. Janssen, Leuven, both of (BE); Philip A. Ruziska, Kingwood, TX (US)

(73) Assignee: ExxonMobil Chemical Patents, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/073,148

(22) Filed: May 5, 1998

(51) Int. Cl.[7] .............................. C07C 4/06; C07C 4/02
(52) U.S. Cl. ...................... 585/653; 585/648; 585/644; 585/650; 585/651
(58) Field of Search ................ 585/648, 644, 585/650, 651, 653; 208/113, 114, 118, 120.01

(56) References Cited

U.S. PATENT DOCUMENTS

| | | | | |
|---|---|---|---|---|
| 3,929,625 A | * | 12/1975 | Lucas | 208/188 |
| 4,440,871 A | | 4/1984 | Lok et al. | 502/214 |
| 4,456,454 A | * | 6/1984 | Jenkins, Jr. | 44/73 |
| 4,666,875 A | * | 5/1987 | Pellet et al. | 502/65 |
| 4,842,714 A | | 6/1989 | Pellet et al. | 208/114 |
| 4,973,764 A | * | 11/1990 | Oswald et al. | 568/649 |
| 4,980,053 A | | 12/1990 | Li et al. | 208/120 |
| 5,053,573 A | * | 10/1991 | Jorgensen et al. | 585/475 |
| 5,232,675 A | | 8/1993 | Shu et al. | 423/328 |
| 5,318,696 A | * | 6/1994 | Kowalski | 208/120 |
| 5,326,465 A | | 7/1994 | Yongqing et al. | 208/120 |
| 5,358,918 A | | 10/1994 | Yukang et al. | 502/67 |
| 5,366,948 A | | 11/1994 | Absil et al. | 502/68 |
| 5,380,690 A | | 1/1995 | Zhicheng et al. | 502/65 |
| 5,456,821 A | | 10/1995 | Absil et al. | 208/114 |
| 5,675,050 A | | 10/1997 | Des Couriers et al. | 585/533 |
| 5,846,403 A | * | 12/1998 | Swan et al. | 208/113 |
| 5,914,433 A | * | 6/1999 | Marker | 585/313 |
| 6,288,298 B1 | * | 9/2001 | Rodriguez et al. | 585/648 |

FOREIGN PATENT DOCUMENTS

| | | | |
|---|---|---|---|
| EP | 142156 A | * | 5/1985 |
| EP | 142156 A | * | 6/1990 |
| EP | 395345 A | * | 10/1990 |
| WO | WO 91/18851 | | 12/1991 |

* cited by examiner

Primary Examiner—Thuan D. Dang

(57) ABSTRACT

The invention provides a method for converting an olefinic hydrocarbon feedstock to propylene comprising: contacting a hydrocarbon feedstock under catalytic cracking conditions with a catalyst comprising a catalyst selected from the group consisting of SAPO catalysts, MeAPO catalysts, MeASPO catalysts, ElAPO catalysts, ElASPO catalysts, rare earth exchanged catalysts from any of the preceding groups, and mixtures thereof, under cracking conditions to selectively produce propylene. The invention further provides a method for stabilizing a catalyst to steam from the foregoing group by ion exchange with a rare earth metal. A catalyst has enhanced stability as used herein when treated with a rare earth metal or metals in a concentration effective to provide a catalyst which exhibits a higher conversion of a hydrocarbon feedstock to propylene than does an equal quantity of an untreated sample of the same catalyst under the same conditions following exposure of each catalyst to steam for a period of at least 10 hours.

34 Claims, No Drawings

METHOD FOR SELECTIVELY PRODUCING PROPYLENE BY CATALYTICALLY CRACKING AN OLEFINIC HYDROCARBON FEEDSTOCK

FIELD OF THE INVENTION

The invention relates to catalytic cracking of hydrocarbons. Particularly the invention relates to a method providing improved selectivity for cracking hydrocarbon feedstocks to propylene by contacting the hydrocarbon under cracking conditions with a catalyst selected from the nonzeolitic molecular sieves consisting of silicoaluminophosphates ("SAPO"), metal aluminophosphates ("MeAPO"), metal aluminosilicophosphates ("MeASPO") elemental aluminophosphates ("ElAPO") and elemental aluminosilicophosphates ("ElASPO") where the metals include divalent Co, Fe, Mg, Mn, and Zn and trivalent Fe and the elements include Li, Be, B, Ga, Ge, As, and Ti.

BACKGROUND OF THE INVENTION

Thermal and catalytic conversion of hydrocarbons to olefins is an important industrial process producing millions of pounds of olefins each year. Because of the large volume of production, small improvements in operating efficiency translate into significant profits. Catalysts play an important role in more selective conversion of hydrocarbons to olefins.

While important catalysts are found among the natural and synthetic zeolites, it has also been recognized that non-zeolitic molecular sieves such as silicoaluminophosphates (SAPO) including those described in U.S. Pat. No. 4,440,871 also provide excellent catalysts for cracking to selectively produce light hydrocarbons and olefins. The SAPO molecular sieve has a network of $AlO_4$, $SiO_4$, and $PO_4$ tetrahedra linked by oxygen atoms. The negative charge in the network is balanced by the inclusion of exchangeable protons or cations such as alkali or alkaline earth metal ions. The interstitial spaces or channels formed by the crystalline network enables SAPOs to be used as molecular sieves in separation processes and in catalysis. There are a large number of known SAPO structures. The synthesis and catalytic activity of the SAPO catalysts are disclosed in U.S. Pat. No. 4,440,871.

In other crystalline microporous solids belonging to the class of aluminophosphates the framework is normally neutral (Al (III):P (V) atomic ratio =1). This framework can be made negative and thereby gives these materials advantageous properties such as adsorption, cation exchange or catalytic activity by replacing P(V) or the pair Al (III), P (V) with a tetravalent element such as silicon, converting to the closely related SAPO structure discussed above, or by replacing Al (III) with a metal, especially a divalent metal such as zinc or cobalt, the materials obtained being denoted by the acrornym MeAPO where Me is the metal, or else by combining these two types of substitution the materials obtained being denoted by the acronym MeAPSO. A group of such materials is described in U.S. Pat. No. 5,675,050.

In the International Application WO 91/18851 that exchange of cations to provide Lewis acid sites in zeolite and SAPO catalytic structures in isomerization catalysts is disclosed. SAPO-11 is disclosed as being particularly effective in this system. The application focuses on skeletal isomerization of n-olefins. There is no teaching of enhanced selectivity or stability under catalytic cracking conditions. Nor is there any discussion of increased stability in rare earth exchanged SAPO.

SAPO catalysts mixed with zeolites (including rare earth exchanged zeolites) are known to be useful in cracking of gasoils (U.S. Pat. No. 5,318,696). U.S. Pat. Nos. 5,456,821 and 5,366,948 describe cracking catalysts with enhanced propylene selectivity which are mixtures of phosphorus treated zeolites with a second catalyst which may be a SAPO or a rare earth exchanged zeolite. Rare earth treated zeolite catalysts useful in catalytic cracking are disclosed in U.S. Pat. Nos. 5,380,690, 5,358,918, 5,326,465, 5232,675 and 4,980,053. The use of SAPO catalysts for cracking crude oil feed or "carbon-hydrogen fragmentation compounds" (materials with 5 or less carbons) is disclosed in U.S. Pat. Nos. 4,666,875 and 4,842,714 (SAPO-37 preferred for cracking gas oils). Although these patents disclose the use of rare earth exchanged SAPO catalysts, they state: "At present the presence of rare earth cations with the SAPO molecular sieves has not been observed to be beneficial to the activity of the SAPO component. The exact nature of the relationship of multi-valent cations and SAPO catalysts is not clearly understood at present, although in some instances their presence may be beneficial." (U.S. Pat. No. 4,666,875 at Col. 4 Lines 39–44, U.S. Pat. No. 4,842,714 Col. 11, Lines 29–34.)

The art has not previously recognized the highly selective conversion of hydrocarbon, especially naphtha feedstocks to propylene promoted by SAPO and related catalysts nor the improved stability obtained by rare earth exchanging such catalysts.

SUMMARY OF THE INVENTION

The invention provides a method for converting an olefinic hydrocarbon feedstock to propylene comprising: contacting a hydrocarbon feedstock under catalytic cracking conditions with a catalyst comprising a nonzeolitic catalyst selected from the group consisting of SAPO catalysts, MeAPO catalysts, MeASPO catalysts, ElAPO catalysts, ElASPO catalysts, rare earth exchanged catalysts from any of the preceding groups, and mixtures thereof, under cracking conditions to selectively produce propylene. Preferably the method is carried out to produce propylene in a propylene to ethylene ratio of at least 4:1 and a propylene to butylene, ration of at least 2:1. The invention further provides a method for stabilizing a catalyst from the foregoing group by ion exchange with a rare earth metal. A catalyst has enhanced stability as used herein when treated with a rare earth metal or metals in a concentration effective to provide a catalyst which exhibits a higher conversion of a hydrocarbon feedstock to propylene than does an equal quantity of an untreated sample of the same catalyst under the same conditions following exposure of each catalyst to steam for a period of at least 10 hours. The invention also provides an improvement in methods for catalytic cracking of an olefinic hydrocarbon feedstock to produce a light olefin containing product wherein it is desired to improve the propylene content of the product mixture. The improvement comprises mixing a catalyst selected from the non zeolitic catalyst group consisting of SAPO catalysts, MeAPO catalysts, MeASPO catalysts, ElAPO catalysts and ElASPO catalysts with a second cracking catalyst in a quantity sufficient to increase propylene content in the light olefin product while decreasing either ethylene or butylene when the product composition obtained with the mixed catalyst is compared to the product composition obtained with the second catalyst alone under the same reaction conditions.

DETAILED DESCRIPTION OF THE INVENTION

The silicoaluminophosphate (SAPO) catalysts useful in the present invention have a three-dimensional microporous crystal framework structure of $PO_2^+$, $AlO_2^-$ and $SiO_2$ tetrahedral units, and whose essential empirical chemical composition on an anhydrous basis is: m R:(Si[x]Al[y]P[z])O[2] wherein "R" represents at least one organic templating agent present in the intracrystalline pore system: "m" represents the moles of "R" present per mole of (Si[x]Al[y]P[z])O2 and has a value of from zero to 0.3, the maximum value in each case depending upon the molecular dimensions of the templating agent and the available void volume of the pore system of the particular silicoaluminophosphate species involved, "x", "y" and "z" represent the mole fractions of silicon, aluminum and phosphorus, respectively, present as tetrahedral oxides, representing the following values for "x", "y" and "z".

| Mole Fraction | | |
|---|---|---|
| x | y | z |
| 0.01 | 0.47 | 0.52 |
| 0.94 | 0.01 | 0.05 |
| 0.98 | 0.01 | 0.01 |
| 0.39 | 0.60 | 0.01 |
| 0.01 | 0.60 | 0.39 |

When synthesized in accordance with the process disclosed in U.S. Pat. No. 4,440,871, the minimum value of "m" y in the formula above is 0.02. In a preferred sub-class of the SAPOs useful in this invention, the values of "x", "y" and "z"in the formula above are set out in the following table:

| Mole Fraction | | |
|---|---|---|
| x | y | z |
| 0.02 | 0.49 | 0.49 |
| 0.25 | 0.37 | 0.38 |
| 0.25 | 0.48 | 0.27 |
| 0.13 | 0.60 | 0.27 |
| 0.02 | 0.60 | 0.38 |

Preferred SAPO catalysts include SAPO-11, SAPO-17, SAPO-31, SAPO-34, SAPO-35, SAPO-41, and SAPO-44.

The catalysts suitable for use in the present invention include, in addition to the SAPO catalysts, the metal integrated aluminophosphates (MeAPO and ElAPO) and metal integrated silicoaluminophosphates (MeAPSO and ElAPSO). The MeAPO, MeAPSO, ElAPO, and ElAPSO families have additional elements included in their framework. For example, Me represents the elements Co, Fe, Mg, Mn, or Zn, and El represents the elements Li, Be, Ga, Ge, As, or Ti. Preferred catalysts include MeAPO-11, MeAPO-31, MeAPO-41, MeAPSO-11, MeAPSO-31, and MeAPSO-41, MeAPSO-46, ElAPO-11, ElAPO-31, ElAPO-41, ElAPSO-11, ElAPSO-31, and ElAPSO-41.

The non-zeolitic SAPO, MeAPO, MeAPSO, ElAPO and ElAPSO classes of microporous, materials are further described in the "Atlas of Zeolite Structure Types" by W. M. Meier, D. H. Olson and C. Baerlocher (4th ed.; Butterworths/Intl. Zeolite Assoc. (1996) and "Introduction to Zeolite Science and Practice", H. Van Bekkum, E. M. Flanigen and J. C. Jansen Eds., Elsevier, N.Y., (1991).).

The selected catalysts may also include cations selected from the group consisting of cations of Group IIA, Group IIIA, Groups IIIB to VIIB and rare earth cations selected from the group consisting of cerium, lanthanum, praseodymium, neodymium, promethium, samarium, europium, gadolinium, terbium, dysprosium, holmium, erbium, thulium, ytterbium, lutetium and mixtures thereof.

Preferred olefinic hydrocarbon feedstocks are nathphas in the boiling range of 18° to 220° C. (65° F. to 430° F.). The naphthas may be thermally cracked naphthas or catalytically cracked naphthas. The feed should contain from at least 10 wt % to about 70 wt % olefins, preferably 20 wt % to 70 wt %, and may also include naphthenes and aromatics. The naphthas may contain paraffins in the range of 5 wt % to 35 wt %, preferably 10 wt % to 30 wt %, most preferably 10 wt % to 25 wt %. For example, the naphtha may be derived from fluid catalytic cracking ("FCC") of gas oils and resids, or from delayed or fluid coking of resids. The preferred naphtha streams are derived from FCC gas oils or resids which are typically rich in olefins and diolefins and relatively lean in paraffins.

Catalytic cracking conditions mean a catalyst contacting temperature in the range of about 400° C. to 750° C., more preferably in the range of 450° C. to 700° C., most preferably in the range of 500° C. to 650° C. The catalyst contacting process is preferably carried out at a weight hourly space velocity (WHSV) in the range of about 0.1 $Hr^{-1}$ to about 300 $Hr^{-1}$, more preferably in the range of about 1.0 $Hr^{-1}$ to about 250 $Hr^{1-}$, and most preferably in the range of about 10 $Hr^{-1}$ to about 100 $Hr^{-1}$. Pressure in the contact zone may be from 0.1 to 30 atm. absolute, preferably 1 to 3 atm. absolute, most preferably about 1 atm. absolute. The catalyst may be contacted in any reaction zone such as a fixed bed, a moving bed, a slurry, a transfer line, a riser reactor or a fluidized bed.

Test Conditions

A series of runs in a small bench reactor was conducted on hexene as a model compound. Comparison runs with a ZSM-5 zeolite catalyst commercially available from Intercat. Inc., of Sea Girt, New Jersey were conducted over a fixed bed of catalyst. The effluent stream was analyzed by on-line gas chromatography. A column having a length of 60 m packed with fused silica was used for the analysis. The gas chromatograph was a dual flame ionization detector equipped Hewlett-Packard Model 5880. All tabulated data is in weight per cent unless otherwise indicated.

EXAMPLE 1

Constant Reactor Conditions

The hexene model compound was cracked over ZSM-5, SAPO-11 and SAPO-34 catalysts at 650° C., 12hr$^{-1}$ WHSV, 1.6 nitrogen dilution, 12 psig.

TABLE 1

| Catalyst | ZSM-5 | SAPO-34 | SAPO-11 |
|---|---|---|---|
| Conversion | 95.4 | 63.6 | 88.8 |
| Key Results | | | |
| Ethylene | 24.5 | 11.0 | 8.4 |
| Propylene | 35.8 | 30.3 | 54.8 |
| Butylenes | 12.8 | 11.2 | 11.8 |
| Aromatics | 12.8 | 2.7 | 8.5 |
| Light Saturates | 9.5 | 8.5 | 5.4 |
| Selectivity | | | |
| (% of Conversion) | | | |
| Ethylene | 25.7 | 17.3 | 9.5 |
| Propylene | 37.5 | 47.6 | 61.7 |
| Butylene | 13.4 | 17.6 | 13.3 |

TABLE 1-continued

| Catalyst | ZSM-5 | SAPO-34 | SAPO-11 |
| --- | --- | --- | --- |
| Propylene/ethylene | 1.5 | 2.8 | 6.5 |
| Propylene/butylene | 2.8 | 2.7 | 4.7 |

As can be seen from Table 1, the SAPO-11 catalyst was slightly less active than the comparison ZSM-5 in terms of conversion. The data show that SAPO-11 was more selective for propylene over ethylene and butylene as ZSM-5, and SAPO-34 also shows significantly increased production of propylene over both ethylene and butylene.

EXAMPLE 2

Constant Conversion

In this example the conditions are the same as in Example 1 except the weight hourly space velocity was adjusted to make conversion equal for the control ZSM-5 and SAPO-11.

TABLE 2

| Catalyst | ZSM-5 | SAPO-11 |
| --- | --- | --- |
| WHSV, $Hr^{-1}$ | 40 | 12 |
| Conversion | 89.0 | 88.8 |
| Key Results | | |
| Ethylene | 13.1 | 8.4 |
| Propylene | 47.6 | 54.8 |
| Butylene | 14.9 | 11.8 |
| Aromatics | 7.4 | 8.5 |
| Light Saturates | 6.1 | 5.4 |
| Selectivity | | |
| Ethylene | 14.7 | 9.5 |
| Propylene | 53.3 | 61.7 |
| Butylene | 16.7 | 13.3 |
| Propylene/Ethylene Ratio | 3.6 | 6.5 |
| Propylene/Butylene Ratio | 3.2 | 4.7 |

As can be seen from Table 2, SAPO-11 produced significantly more propylene and less ethylene and butylenes than ZSM-5 catalyst.

EXAMPLE 3

Effect of Temperature and Throughput

In this example SAPO-11 extrudate catalyst was tested with the hexene model compound in the apparatus of Example 1 under the conditions indicated in Table 3.

TABLE 3

| Temperature, °C. | 650 | 600 | 600 |
| --- | --- | --- | --- |
| WHSV, $Hr^{-1}$ | 12 | 12 | 8 |
| Conversion | 88.8 | 75.9 | 87.9 |
| Key Results | | | |
| Ethylene | 8.4 | 3.6 | 3.9 |
| Propylene | 54.8 | 60.6 | 69.7 |
| Butylene | 11.8 | 7.1 | 7.4 |
| Aromatics | 8.5 | 2.7 | 5.0 |
| Light Saturates | 5.4 | 1.8 | 2.0 |
| Selectivity, % | | | |
| Ethylene | 9.5 | 4.7 | 4.4 |
| Propylene | 61.7 | 79.8 | 79.3 |
| Butylene | 13.3 | 9.4 | 8.4 |
| Propylene/Ethylene Ratio | 6.5 | 16.8 | 17.9 |
| Propylene/Butylene Ratio | 4.7 | 8.5 | 9.4 |

As the data above indicate, selectivity is improved by reducing the temperature and by maintaining high conversion by decreasing throughput thus increasing the average time the feedstock is in contact with the catalyst. The propylene/ethylene ratio approaching 18:1 is exceptional as is the propylene/butylene ratio at 9.4:1. With ZSM-5 catalysts lowering the temperature typically results in increasing butylene selectivity, while the SAPO catalysts display the opposite trend which is unexpected. It has been found that the selectivity of the catalysts can be maintained over a wide range of conversion levels so long as cracking conditions are maintained.

EXAMPLE 4

Selectivity in Cracking of a Typical Refinery Feedstock

A typical refinery feedstock, Baton Rouge Light Cat. Naphtha, (LCN) was contacted with fresh and steamed SAPO-11 at 600° C., 6 $Hr^{-1}$ WHSV, 1.6 $N_2$ dilution, and 12 psig. The results are listed in Table 4.

TABLE 4

| Catalyst | ZSM-5 | SAPO-11 | SAPO-11 |
| --- | --- | --- | --- |
| Presteaming Conditions | 816° C./40 Hr. | Fresh | 593° C./16 Hr. |
| Conversion | 40.7 | 33.9 | 33.2 |
| Key Results | | | |
| Ethylene | 5.1 | 3.2 | 2.6 |
| Propylene | 24.7 | 24.9 | 25.3 |
| Butylene | 9.5 | 4.2 | 3.8 |
| Aromatics | 4.5 | 5.5 | 4.4 |
| Light Saturates | 1.4 | 1.6 | 1.5 |
| Selectivity, % | | | |
| Ethylene | 12.5 | 9.4 | 7.8 |
| Propylene | 60.7 | 73.5 | 76.2 |
| Butylenes | 23.3 | 12.4 | 11.4 |
| Propylene/Ethylene Ratio | 4.8 | 7.8 | 9.7 |
| Propylene/Butylene Ratio | 2.6 | 5.9 | 6.6 |

The selectivity observed with the model compound is maintained with the refinery feedstock. Selectivity appears to improve when the catalyst is pre-steamed.

EXAMPLE 5

Performance of Calcium Exchanged SAPO-11

To 10 g SAPO-11 was added 1000 ml of a 10 wt % $Ca(NO_3)_2$ solution. This solution was stirred for 16 hrs at 65° C. After washing, the sample was dried overnight at 90° C., followed by air calcination for 16 hrs at 525° C. The procedure was repeated twice to obtain the finished catalyst. The calcium exchanged SAPO-11 was contacted with the hexene model compound at 600° C., and $2Hr^{-1}$. The nitrogen diluent to hydrocarbon ratio was 5:1. The results are shown in Table 5.

TABLE 5

| Catalyst | ZSM-5 | SAPO-11 |
| --- | --- | --- |
| Conversion | 99.3 | 89.8 |
| Key Results | | |
| Ethylene | 20.4 | 4.3 |
| Propylene | 22.6 | 57.5 |
| Butylenes | 8.3 | 11.8 |
| Aromatics | 25.0 | 1.4 |
| Selectivity, % | | |
| Ethylene | 20.5 | 4.8 |
| Propylene | 22.8 | 64.0 |

TABLE 5-continued

| Catalyst | ZSM-5 | SAPO-11 |
|---|---|---|
| Butylenes | 8.4 | 13.1 |
| Propylene/Ethylene Ratio | 1.1 | 13.4 |
| Propylene/Butylene Ratio | 2.7 | 2.9 |

As demonstrated by the data above Ca SAPO-11 was found to be very selective for propylene with a propylene selectivity of 64% and low production of both ethylene and butylenes. An additional benefit is the low aromatics production of only 1.4%.

EXAMPLE 6
Improved Stability With Rare Earth Treated Nonzeolitic Catalyst

SAPO-11 treated with a rare earth (lanthanum) resists loss of activity, when subjected to prolonged exposure to steam. Most zeolite and other molecular sieve catalysts display a characteristic loss of activity when exposed to steam over a prolonged period. As the data below demonstrate rare earth treatment of catalyst (SAPO- 11) produces a catalyst with 60–70% improvement in catalyst activity relative to non-treated SAPO-11 while retaining the outstanding selectivity for propylene over both ethylene and butylene observed in the examples above. A sample of SAPO-11 was ion-exchanged with a lanthanum solution by suspending 10 grams of SAPO-11 in 100 grams of water and 5 grams of $LaCl_3 \cdot 6H_2O$ were added. The mixture was refluxed at 100° C. for 4 hrs, then dried and calcined.

The exchanged catalyst was contacted with Baton Rouge Light Cat Naphtha, at 500° C., 1/1 steam to hydrocarbon weight ratio, at 5 $Hr^{-1}$, 12 psig in the apparatus of Example 1. The steamed catalysts were treated at 760° C. with 100% steam for 16 hours prior to the cracking test. The results are shown in Table 6 below.

TABLE 6

| Catalyst | Fresh SAPO-11 | Steamed SAPO-11 | Steamed LaSAPO-11 |
|---|---|---|---|
| Conversion | 27.5 | 12.0 | 20.2 |
| Key Results | | | |
| Ethylene | 1.5 | 0.4 | 0.9 |
| Propylene | 23.1 | 10.0 | 17.0 |
| Butylene | 2.7 | 1.5 | 2.1 |
| Aromatics | 2.9 | 2.1 | 2.7 |
| Light Saturates | | | |
| Selectivity, % | | | |
| Ethylene | 5.5 | 3.3 | 4.4 |
| Propylene | 84.0 | 83.1 | 84.0 |
| Butylene | 9.8 | 12.5 | 10.4 |
| Propylene/Ethylene Ratio | 15.2 | 25.2 | 19.1 |
| Propylene/Butylenes Ratio | 8.5 | 6.6 | 8.1 |

The preceding data show a positive result of rare earth treatment of a SAPO catalyst. The improved resistance to loss of activity on exposure to steam allows prolonged use of the catalyst. The foregoing results are provided to illustrate the operation of the invention in some of its embodiments. The examples are provided by way of illustration and not as limitations on the scope or practice of the invention, which is defined and limited by the following claims.

We claim:

1. A method of converting an olefinic hydrocarbon feedstock to propylene comprising: contacting the olefinic hydrocarbon feedstock that consists essentially of hydrocarbons boiling in the range of 18° to 148° C. (65° F. to 300° F.) under catalytic cracking conditions with a non-zeolitic catalyst selected from the group consisting of SAPO-11, SAPO-35, SAPO-41, SAPO44, MeAPO-11, MeAPO-31, MeAPO41, MeASPO-11, MeASPO-31, MeASPO41, MEASPO-46, ElAPO-11, El-APO-31, ElAPO-41, ElASPO-11, ElASPO-31, and ElASPO-41, under cracking conditions to selectively produce propylene, at a propylene to butylene ratio of at least 2:1.

2. The method of claim 1, wherein the selectivity produces a propylene to ethylene ratio of at least 4:1.

3. The method of claim 1 wherein the olefinic hydrocarbon feedstock comprises from about 10 wt % to about 70 wt % olefins.

4. The method of claim 1 wherein the olefinic hydrocarbon feedstock comprises from 20 wt % to 70 wt % olefins.

5. The method of claim 1 wherein the olefinic hydrocarbon feedstock comprises from about 5 wt % to about 35 wt % paraffins.

6. The method of claim 1 wherein the olefinic hydrocarbon feedstock comprises from 10 wt % to about 30 wt % paraffins.

7. The method of claim 1 wherein the olefinic hydrocarbon feedstock comprises from about 10 wt % to about 25 wt % paraffins.

8. The method of claim 1 wherein the olefinic hydrocarbon feedstock is contacted with the catalyst at a temperature in the range of 400° C. to 700° C.

9. The method of claim 1 wherein the olefinic hydrocarbon feedstock is contacted with the catalyst at a WHSV of 1 to 300 $hr^{-1}$.

10. The method of claim 1 wherein the olefinic hydrocarbon feedstock is contacted with the catalyst at a pressure of 0.1 to 30 atm. absolute.

11. The method of claim 1 wherein the catalyst is ion exchanged with a solution comprising an alkaline earth metal ion or a rare earth metal ion.

12. The method of claim 1 wherein the catalyst is exchanged against a solution comprising a rare earth metal ion selected from the group consisting of cerium, lanthanum, praseodymium, neodymium, promethium, samarium, europium, gadolinium, terbium, dysprosium, holmium, erbium, thulium, ytterbium, lutetium and mixtures thereof.

13. The method of claim 12 wherein the rare earth metal ion comprises lanthanum.

14. The method in claim 1 wherein the olefinic hydrocarbon feed is cracked over the catalyst at reactor temperatures of from about 400–700° C., pressures of from about 0.1 atmosphere to about 30 atmospheres absolute, and weight hourly space velocities of from about 0.1 $hr^{-1}$ to about 100 $hr^{-1}$.

15. In a method for catalytic cracking of an olefin hydrocarbon feed that consists essentially of hydrocarbons boiling in the range of 18° to 148° C. (65°F. to 300° F.) to produce propylene, the improvement which comprises mixing a first catalyst selected from the non zeolitic silicoaluminophosphate catalyst group consisting of SAPO-11, SAPO-35, SAPO-41, SAPO-44, MeAPO-11, MeAPO-31, MeAPO-41, MeASPO-11, MeASPO-31, MeASPO-41, MeASPO-46, ElAPO-11, ElAPO-31, ElAPO41, ElASPO-11, ElASPO-31 and ElASPO-41 with a second cracking catalyst to form a mixed catalyst system, where the first catalyst is present in a quantity sufficient to increase propylene content in the light olefin containing product while decreasing either ethylene or butylene when the olefinic hydrocarbon feed is contacted with the mixed catalyst system under cracking conditions, compared to a product composition obtained with the second cracking catalyst alone under the same conditions, and where propylene is selectively produced at a propylene to butylene ratio of at least 2:1.

16. The method of claim 15 wherein the olefinic hydrocarbon feedstock comprises from about 10 wt % to about 70 wt % olefins.

17. The method of claim 15 wherein the olefinic hydrocarbon feedstock comprises from 20 wt % to 70 wt % olefins.

18. The method of claim 15 wherein the olefinic hydrocarbon feedstock comprises from about 5 wt % to about 35 wt % paraffins.

19. The method of claim 15 wherein the olefinic hydrocarbon feedstock comprises from about 10 wt % to about 30 wt % paraffins.

20. The method of claim 15 wherein the olefinic hydrocarbon feedstock comprises from about 10 wt % to about 25 wt % paraffins.

21. The method of claim 15 wherein the olefinic hydrocarbon feedstock is contacted with the mixed catalyst system at a temperature in the range of 400° C. to 700° C.

22. The method of claim 15 wherein the olefinic hydrocarbon feedstock is contacted with the mixed catalyst system is contacted at a WHSV of 1 $hr^{-1}$ to 300 $hr^{-1}$.

23. The method of claim 15 wherein the olefinic hydrocarbon feedstock is contacted with the mixed catalyst system is contacted at a pressure of 0.1 to 30 atm absolute.

24. The method of claim 15 wherein the first catalyst is ion exchanged with an aqueous solution comprising an alkaline earth metal ion or a rare earth metal ion.

25. The method of claim 24 wherein the first catalyst is exchanged against a solution comprising a rare earth metal ion selected from the group consisting of cerium, lanthanum, praseodymium, neodymium, promethium, samarium, europium, gadolinium, terbium, dysprosium, holmium, erbium, thulium, ytterbium, lutetium and mixtures thereof.

26. The method of claim 24 wherein the rare earth metal ion comprises lanthanum.

27. The method in claim 18 wherein the olefinic hydrocarbon feed is cracked over the catalyst at reactor temperatures of from about 400–700° C., pressures of from about 0.1 atmosphere to about 30 atmospheres absolute, and weight hourly space velocities of from about 0.1 $hr^{-1}$ about 100 $hr^{-1}$.

28. A method for producing propylene in a cracking process while minimizing production of butylene which comprises contacting an olefinic hydrocarbon feed that consists essentially of hydrocarbons boiling in the range of 18° to 148° C. (65° F. to 300° F.) with a non-zeolitic silicoaluminophosphate containing catalyst selected from the group consisting of SAPO-11, SAPO-35, SAPO-41, SAPO44, MeAPO-11, MeAPO-31, MeAPO-41, MeASPO-11, MeASPO-31, MeASPO-41, MeASPO46, ElAPO-11, ElAPO-31, ElAPO41, ElASPO-11, ElASPO-31 and ElASPO41, under cracking conditions to produce at least 2 times as much propylene as butylenes.

29. A method according to claim 28 wherein the process produces at least 4 times as much propylene as ethylene.

30. A method according to claim 28 wherein at least 2.5 times as much propylene as butylenes is produced.

31. A method according to claim 28 wherein at least 3 times as much propylene as butylenes is produced.

32. A method for producing propylene in a cracking process while minimizing production of ethylene which comprises contacting an olefinic hydrocarbon feed that consists essentially of hydrocarbons boiling in the range of 18° to 148° C. (65° F. to 300° F.) with a non-zeolitic silicoaluminophosphate containing catalyst selected from the group consisting SAPO-11, SAPO-35, SAPO41, SAPO-44, MeAPO-11, MeAPO-31, MeAPO-41, MeASPO-11, MeASPO-31, MeASPO-41, MeASPO-46, ElAPO-11, ElAPO-31, ElAPO-41, ElASPO-11, ElASPO-31 and ElASPO41, under cracking conditions to produce at least 2 times as much propylene as ethylene and at least two times as much propylene as butylenes.

33. A method according to claim 32 wherein the process produces at least 4 times as much propylene as ethylene.

34. A method according to claim 32 wherein at least 3 times as much propylene as butylenes is produced.

* * * * *